(12) United States Patent
Polidori et al.

(10) Patent No.: US 7,654,955 B2
(45) Date of Patent: Feb. 2, 2010

(54) APPARATUS AND METHODS FOR ASSESSING METABOLIC SUBSTRATE UTILIZATION

(75) Inventors: David Polidori, Portola Valley, CA (US); Kevin Hall, Columbia, MD (US)

(73) Assignee: Entelos, Inc., Foster City, CA (US)

( * ) Notice: Subject to any disclaimer, the term of this patent is extended or adjusted under 35 U.S.C. 154(b) by 984 days.

(21) Appl. No.: 10/995,030

(22) Filed: Nov. 19, 2004
(Under 37 CFR 1.47)

(65) Prior Publication Data
US 2005/0197785 A1    Sep. 8, 2005

Related U.S. Application Data

(60) Provisional application No. 60/523,646, filed on Nov. 19, 2003.

(51) Int. Cl.
*A61B 5/00* (2006.01)
(52) U.S. Cl. .................. 600/300; 600/345; 600/347; 600/365
(58) Field of Classification Search .................. None
See application file for complete search history.

(56) References Cited

U.S. PATENT DOCUMENTS

| | | |
|---|---|---|
| 5,657,255 A | 8/1997 | Fink et al. |
| 5,808,918 A | 9/1998 | Fink et al. |
| 5,914,891 A | 6/1999 | McAdams et al. |
| 5,930,154 A | 7/1999 | Thalhammer-Reyero |
| 5,947,899 A | 9/1999 | Winslow et al. |
| 5,995,860 A | 11/1999 | Sun et al. |
| 6,051,029 A | 4/2000 | Paterson et al. |
| 6,069,629 A | 5/2000 | Paterson et al. |
| 6,078,739 A | 6/2000 | Paterson et al. |

(Continued)

FOREIGN PATENT DOCUMENTS

WO    WO 99/27443    6/1999

(Continued)

OTHER PUBLICATIONS

Bendetti et al., "Body composition and energy expenditure after weight loss following bariatric surgery," *J. Am. Coll. Nutr.* 19(2):270-4 (2000).

(Continued)

*Primary Examiner*—Robert L Nasser
(74) *Attorney, Agent, or Firm*—Karen E. Flick

(57) ABSTRACT

Apparatus and methods for assessing metabolic substrate utilization are described. In one embodiment, a processor-readable medium includes code to receive data indicative of a plasma glucose concentration, a plasma free fatty acid concentration, and a respiratory quotient of a subject. The processor-readable medium also includes code to calculate, based on the data, respective values of a set of metabolic parameters. The set of metabolic parameters includes a first metabolic parameter and a second metabolic parameter. The value of the first metabolic parameter is indicative of whether the subject has a predisposition towards oxidation of a first type of metabolic substrate or a second type of metabolic substrate, and the value of the second metabolic parameter is indicative of the subject's responsiveness to a change in availability of the first type of metabolic substrate or the second type of metabolic substrate.

16 Claims, 7 Drawing Sheets

U.S. PATENT DOCUMENTS

| | | |
|---|---|---|
| 6,108,635 A | 8/2000 | Herren et al. |
| 2001/0032068 A1 | 10/2001 | Paterson et al. |
| 2002/0091666 A1 | 7/2002 | Rice et al. |
| 2002/0193979 A1 | 12/2002 | Paterson et al. |
| 2003/0009099 A1 | 1/2003 | Lett et al. |
| 2003/0018457 A1 | 1/2003 | Lett et al. |
| 2003/0033127 A1 | 2/2003 | Lett |
| 2003/0058245 A1 | 3/2003 | Brazhnik et al. |
| 2003/0208133 A1 | 11/2003 | Mault |

FOREIGN PATENT DOCUMENTS

| | | |
|---|---|---|
| WO | WO 00/63793 | 10/2000 |
| WO | 00/65523 | 11/2000 |
| WO | WO 00/65523 | 11/2000 |
| WO | 01/57775 | 8/2001 |
| WO | 01/98935 | 12/2001 |
| WO | 02/44992 | 6/2002 |
| WO | WO 02/097706 | 12/2002 |

OTHER PUBLICATIONS

Blundell et al., "Differences in Postprandial Responses to Fat and Carbohydrate Loads in Habitual High and Low Fat Consumers (Phenotypes)," *British Journal of Nutrition* 88(2):125-132.

Bobbioni-Harsch et al., "Energy expenditures and substrate oxidative patterns, after glucose, fat or mixed load in normal weight subjects," *Eur. J. Clin. Nutr.* 51(6):370-4 (1997).

Bulow et al., "Co-ordination of hepatic and adipose tissue lipid metabolism after oral glucose," *J. Lipid Res.* 40(11):2034-43 (1999).

Dionne et al., "Postexercise Macronutrient Oxidation: a Factor Dependent on Postexercise Macronutrient Intake," *Am J Clin Nutr* 69:927-30 (1999).

McGarry, "Banting Lecture 2001: Dysregulation of Fatty Acid Metabolism in the Etiology of Type 2 Diabetes," *Diabetes* 51:7-18 (2002).

Sjostrand et al., "Delayed transcapillary transport of insulin to muscle interstitial fluid in obese subjects," *Diabetes* 51(9):2742-8 (2002).

Smith et al., "Fat and Carbohydrate Balances During Adaptation to a High Fat Diet," *Am J Clin Nutr* 71:450-7 (2000).

University of Colorado Heath Sciences Center—Center for Human Nutrition, "Effect of Resistant Starch Consumption on Adiposity," http://www.uchsc.edu/nutrition/Higgins/resstarch.htm, printed Oct. 27, 2004.

ically assessed by measuring the respiratory quotient. Although the respiratory quotient can be useful for determining relative rates of carbohydrate oxidation and fat oxidation, the respiratory quotient typically does not provide information regarding the underlying causes of differences in carbohydrate oxidation and fat oxidation. In particular, it is often unclear whether differences in carbohydrate oxidation and fat oxidation are due to differences in availability of carbohydrates and fats or due to a predisposition towards carbohydrate oxidation or fat oxidation.

APPARATUS AND METHODS FOR ASSESSING METABOLIC SUBSTRATE UTILIZATION

CROSS REFERENCE TO RELATED APPLICATION

This application claims the benefit of U.S. Provisional Application No. 60/523,646, entitled "Apparatus and Method for Assessing Substrate Utilization in Patients" and filed on Nov. 19, 2003, the disclosure of which is incorporated herein by reference in its entirety.

FIELD OF THE INVENTION

The field of the invention relates to metabolic substrate utilization. For example, apparatus and methods for assessing metabolic substrate utilization are described.

BACKGROUND OF THE INVENTION

Metabolic substrate utilization can be an important factor in the pathophysiology of certain disorders. In particular, defects in metabolic substrate utilization have been observed in individuals that are suffering from certain metabolic disorders, such as obesity and diabetes. For example, obese individuals and diabetic individuals can have reduced basal fat oxidation rates and reduced postprandial carbohydrate oxidation rates compared to control individuals. Defects in metabolic substrate utilization have also been observed in individuals that are at risk of developing certain metabolic disorders. For example, prediabetic individuals can have similar defects in fat oxidation as diabetic individuals, and this observation has been used to associate defects in fat oxidation with the progression of diabetes. In addition, defects in metabolic substrate utilization have been observed in individuals that are recovering from certain metabolic disorders. For example, previously obese individuals can have lower fat oxidation rates compared to control individuals. Also, these previously obese individuals sometimes do not increase fat oxidation as quickly in response to additional fat intake compared to control individuals.

Metabolic substrate utilization is typically assessed by measuring the respiratory quotient. Although the respiratory quotient can be useful for determining relative rates of carbohydrate oxidation and fat oxidation, the respiratory quotient typically does not provide information regarding the underlying causes of differences in carbohydrate oxidation and fat oxidation. In particular, it is often unclear whether differences in carbohydrate oxidation and fat oxidation are due to differences in availability of carbohydrates and fats or due to a predisposition towards carbohydrate oxidation or fat oxidation.

It is against this background that a need arose to develop the apparatus and methods described herein.

SUMMARY OF THE INVENTION

In one embodiment, a processor-readable medium includes code to receive data indicative of a plasma glucose concentration, a plasma free fatty acid concentration, and a respiratory quotient of a subject. For example, the data can be indicative of the plasma glucose concentration, the plasma free fatty acid concentration, and the respiratory quotient of the subject at a set of measurement times. The processor-readable medium also includes code to calculate, based on the data, respective values of a set of metabolic parameters. For example, the code to calculate the respective values of the set of metabolic parameters can include code to perform a regression analysis on the data. The set of metabolic parameters includes a first metabolic parameter and a second metabolic parameter. The value of the first metabolic parameter is indicative of whether the subject has a predisposition towards oxidation of a first type of metabolic substrate or a second type of metabolic substrate. For example, the value of the first metabolic parameter can be indicative of whether the subject has a predisposition towards oxidation of carbohydrates or fats. The value of the second metabolic parameter is indicative of the subject's responsiveness to a change in availability of the first type of metabolic substrate or the second type of metabolic substrate. For example, the value of the second metabolic parameter can be indicative of the subject's responsiveness to a change in availability of carbohydrates or fats.

In another embodiment, a processor-readable medium includes code to receive data indicative of a blood glucose level, a blood free fatty acid level, and a respiratory quotient of a subject. The processor-readable medium also includes code to calculate, based on the data, a value of a metabolic parameter for the subject. The value of the metabolic parameter is indicative of whether the subject has a predisposition towards carbohydrate oxidation or fat oxidation.

In another embodiment, a method includes receiving a set of measurement results for a subject, the set of measurement results being indicative of a plasma glucose concentration, a plasma free fatty acid concentration, and a respiratory quotient of the subject. The method also includes, based on the set of measurement results, calculating respective values of a set of metabolic parameters. The set of metabolic parameters includes a first metabolic parameter and a second metabolic parameter. The value of the first metabolic parameter is indicative of whether the subject has a predisposition towards oxidation of a first type of metabolic substrate relative to a second type of metabolic substrate, and the value of the second metabolic parameter is indicative of the subject's responsiveness to a change in availability of the first type of metabolic substrate.

In another embodiment, a method includes applying a set of measurements to a subject to produce a set of measurement results for the subject, the set of measurements being configured to evaluate a blood glucose level, a blood free fatty acid level, and a respiratory quotient of the subject. The method also includes, based on the set of measurement results, determining whether the subject has a predisposition towards carbohydrate oxidation or fat oxidation.

In another embodiment, a method includes calculating an untreated value of a metabolic parameter for a subject having a metabolic disorder, the untreated value of the metabolic parameter being indicative of whether the subject has an untreated predisposition towards carbohydrate oxidation or fat oxidation. The method also includes applying a therapy to the subject. The method also includes calculating a treated value of the metabolic parameter for the subject, the treated value of the metabolic parameter being indicative of whether the subject has a treated predisposition towards carbohydrate oxidation or fat oxidation. The method further includes comparing the treated value of the metabolic parameter with the untreated value of the metabolic parameter.

In a further embodiment, a method includes calculating an untreated value of a metabolic parameter for a subject having a metabolic disorder, the untreated value of the metabolic parameter being indicative of the subject's untreated responsiveness to a change in availability of a metabolic substrate. The method also includes applying a therapy to the subject. The method also includes calculating a treated value of the metabolic parameter for the subject, the treated value of the metabolic parameter being indicative of the subject's treated responsiveness to a change in availability of the metabolic substrate. The method further includes comparing the treated value of the metabolic parameter with the untreated value of the metabolic parameter.

Other embodiments of the invention are also contemplated. The foregoing summary and the following detailed description are not meant to restrict the invention to any particular embodiment but are merely meant to describe some embodiments of the invention. Also, it is contemplated that some embodiments described herein may be used interchangeably with one another.

DETAILED DESCRIPTION

Overview

Figure 1:
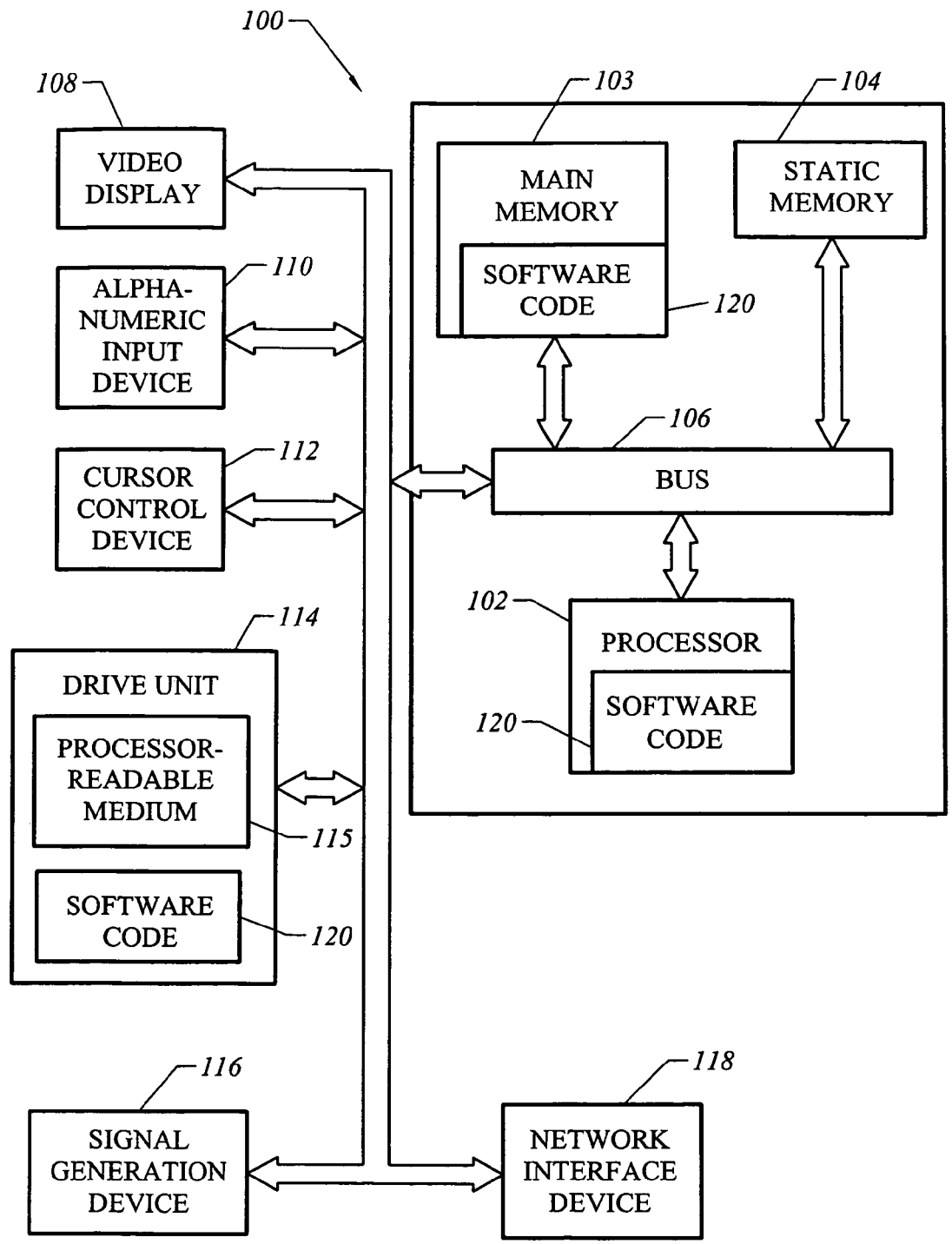
FIG. 1 illustrates a system block diagram of a computer system that can be operated in accordance with some embodiments of the invention.

Embodiments of the invention relate to metabolic substrate utilization. For example, apparatus and methods for assessing metabolic substrate utilization are described. According to some embodiments of the invention, metabolic substrate utilization of a subject is assessed by calculating respective values of a set of metabolic parameters. The set of metabolic parameters can include a first metabolic parameter that characterizes the subject's predisposition towards oxidation of a first type of metabolic substrate or a second type of metabolic substrate. The set of metabolic parameters can also include a second metabolic parameter that characterizes the subject's responsiveness to a change in availability of the first type of metabolic substrate. The set of metabolic parameters can further include a third metabolic parameter that characterizes the subject's responsiveness to a change in availability of the second type of metabolic substrate.

Advantageously, the apparatus and methods described herein can be used to identify characteristics of metabolic substrate utilization that typically cannot be identified based on simply measuring the respiratory quotient. For example, the apparatus and methods described herein can provide information regarding the underlying causes of differences in oxidation of a first type of metabolic substrate and a second type of metabolic substrate. In turn, such information can be used in numerous applications where metabolic substrate utilization plays a role. For example, such information can be used to develop a therapy for treating a metabolic disorder, such as obesity or diabetes.

Terms

The following provides examples of some of the terms described herein. These examples may likewise be expanded upon herein.

As used herein, the singular terms "a", "an", and "the" include plural referents unless the context clearly dictates otherwise.

As used herein, the term "set" refers to a collection of one or more elements. Elements of a set can also be referred to as members of the set. Elements of a set can be the same or different. In some instances, elements of a set can share one or more common characteristics.

As used herein, the term "metabolic substrate" refers to a nutrient from which a biological organism can extract energy. Metabolic substrates can be classified as different types, such as carbohydrates, fats, and proteins. In some instances, a particular type of metabolic substrate can also refer to a component of that type of metabolic substrate or a product derived from that type of metabolic substrate. Thus, for example, carbohydrates can also refer to glucose, and fats can also refer to fatty acids.

As used herein, the term "metabolic substrate utilization" refers to a set of biological processes through which a biological organism can extract energy from a metabolic substrate and can use the energy to maintain life. Typically, energy is extracted from one or more types of metabolic substrates. Metabolic substrate utilization can involve biological processes related to, for example, digestion, absorption, storage, mobilization, and oxidation of metabolic substrates. Metabolic substrate utilization can also involve biological processes related to, for example, energy expenditure based on oxidation of metabolic substrates.

As used herein, the term "metabolic disorder" refers to a defect in or a defect affecting metabolic substrate utilization. Examples of metabolic disorders include obesity and diabetes.

As used herein, the term "subject" refers to a biological organism to which a measurement or a therapy can be applied. A biological organism can be, for example, any warm-blooded animal, such as a human individual or a non-human mammal. In some instances, a subject can have a metabolic disorder. Subjects having a metabolic disorder can include, for example, subjects that have been diagnosed with the metabolic disorder, subjects that exhibit a set of symptoms associated with the metabolic disorder, or subjects that are progressing towards or are at risk of developing the metabolic disorder.

As used herein, the term "respiratory quotient" refers a ratio of an amount of carbon dioxide produced by a biological organism and an amount of oxygen consumed by the biological organism. The amount of carbon dioxide produced and the amount of oxygen consumed typically depend on a particular metabolic substrate being oxidized. For example, oxidation of a molecule glucose typically involves the following relationship: $6O_2 + C_6H_{12}O_6 \Rightarrow 6CO_2 + 6H_2O + 38$ ATP. Thus, when glucose is being oxidized, the respiratory quotient is typically 1.0, since the number of carbon dioxide molecules produced is typically equal to the number of oxygen molecules consumed. The respiratory quotient is also typically 1.0 when other types of carbohydrates are oxidized. The respiratory quotient is typically 0.7 for oxidation of fats and is typically 0.8 for oxidation of proteins. For a mixture of carbohydrates, fats, and proteins, the respiratory quotient is typically in the range of 0.7 to 1, such as from 0.80 to 0.85.

As used herein, the term "therapy" refers to a stimulus or perturbation that can be applied to a biological organism. In some instances, a therapy can affect a biological organism, such that the biological organism can exhibit a response to the therapy. Therapies that can be applied to a biological organism can include, for example, drugs, regimens, or combinations thereof.

As used herein, the term "drug" refers to a compound of any degree of complexity that can affect a biological organism, whether by known or unknown biological mechanisms, and whether or not used therapeutically. Examples of drugs include typical small molecules of research or therapeutic interest; naturally-occurring factors such as endocrine, paracrine, or autocrine factors or factors interacting with cell receptors of any type; intracellular factors such as elements of intracellular signaling pathways; factors isolated from other natural sources; pesticides; herbicides; and insecticides. Drugs can also include, for example, agents used in gene therapy such as DNA and RNA. Drugs can further include, for example, food supplements. Also, antibodies, viruses, bacteria, and bioactive agents produced by bacteria and viruses (e.g., toxins) can be considered as drugs. A response to a drug can be a consequence of, for example, drug-mediated changes in the rate of transcription or degradation of one or more species of RNA, drug-mediated changes in the rate or extent of translational or post-translational processing of one or more polypeptides, drug-mediated changes in the rate or extent of degradation of one or more proteins, drug-mediated inhibition or stimulation of action or activity of one or more proteins, and so forth. In some instances, drugs can exert their effects by interacting with a protein. For certain applications, drugs can also include, for example, compositions including multiple drugs or compositions including a set of drugs and a set of excipients.

As used herein, the term "regimen" refers to a behavioral protocol that can affect a biological organism, whether by known or unknown biological mechanisms, and whether or not used therapeutically. Examples of regimens include meal protocols (e.g., short-term fasting, long-term fasting, single meal per day, multiple meals per day, caloric preload prior to a meal, self-feeding until equilibrium weight is established, and diets with varying metabolic substrate compositions), physical activity or exercise protocols, or a combination thereof.

As used herein, the term "measurement" refers to a test configured to evaluate a characteristic of a biological organism. In some instances, a measurement can refer to an experimental or clinical test that can be applied to a biological organism to produce a measurement result. A measurement can be applied using any of a number of functional, biochemical, and physical techniques appropriate to a particular measurement result being produced. A measurement result can be indicative of, for example, a concentration, a level, a rate, an activity, or any other characteristic of a biological organism. For certain applications, a measurement result can include a value at one or more times; an absolute or relative increase in a value over a time interval; an absolute or relative decrease in a value over a time interval; an average value; a minimum value; a maximum value; a time at minimum value; a time at maximum value; an area below a curve when values are plotted along a given axis (e.g., time); an area above a curve when values are plotted along a given axis (e.g., time); a pattern or trend associated with a curve when values are plotted along a given axis (e.g., time); a rate of change of a value; an average rate of change of a value; a curvature associated with a value; a number of instances a value exceeds, reaches, or falls below another value (e.g., a baseline value) over a time interval; a minimum difference between a value and another value (e.g., a baseline value) over a time interval; a maximum difference between a value and another value (e.g., a baseline value) over a time interval; a normalized value; a scaled value; a statistical measure associated with a value; or a quantity based on a combination, aggregate representation, or relationship of two or more values.

As used herein, the term "biomarker" used in connection with a therapy refers to a characteristic that can be associated with a particular response to the therapy. In some instances, a biomarker of a therapy can refer to a characteristic that can be calculated for a biological organism to infer or predict a particular response of the biological organism to the therapy. Biomarkers can be predictive of different responses to a therapy. For example, biomarkers can be predictive of effectiveness, biological activity, safety, or side effects of a therapy.

Computer System

FIG. 1 illustrates a system block diagram of a computer system 100 that can be operated in accordance with some embodiments of the invention. The computer system 100 includes a processor 102, a main memory 103, and a static memory 104, which are coupled by bus 106. The computer system 100 also includes a video display 108 (e.g., a liquid crystal display ("LCD") or a cathode ray tube ("CRT") display) on which a user-interface can be displayed. The computer system 100 further includes an alpha-numeric input device 110 (e.g., a keyboard), a cursor control device 112 (e.g., a mouse), a disk drive unit 114, a signal generation device 116 (e.g., a speaker), and a network interface device 118. The disk drive unit 114 includes a processor-readable medium 115 storing software code 120 that implements processing according to some embodiments of the invention. The software code 120, or a portion thereof, can also reside within the main memory 103, the processor 102, or both. For certain applications, the software code 120 can be transmitted or received via the network interface device 118.

Methodology for Assessing Metabolic Substrate Utilization

According to some embodiments of the invention, metabolic substrate utilization can be assessed using a methodology that quantitatively relates circulating metabolic substrate levels (e.g., blood levels of metabolic substrates) to metabolic substrate oxidation rates. Metabolic substrate oxidation rates can be represented in absolute terms (e.g., rate of oxidation of a particular type of metabolic substrate in units of mg/min) or in relative terms (e.g., fraction of total energy expenditure associated with oxidation of a particular type of metabolic substrate). The methodology can be associated with a mathematical representation of the competition between carbohydrate oxidation and fat oxidation based on availability of carbohydrates and fats and a set of metabolic parameters. The set of metabolic parameters can include a first metabolic parameter that characterizes a subject's predisposition towards oxidation of carbohydrates or fats. The set of metabolic parameters can also include a second metabolic parameter that characterizes the subject's responsiveness to a change in availability of carbohydrates. The set of metabolic parameters can further include a third metabolic parameter that characterizes the subject's responsiveness to a change in availability of fats.

To capture the effects of availability of carbohydrates and fats and the subject's predisposition and responsiveness, the following equations can be used to characterize the competition between carbohydrate oxidation and fat oxidation:

$$\text{fraction of energy from fat oxidation} = \frac{F^{s_f}}{F^{s_f} + \frac{w}{2} G^{s_g}} \quad \text{(Equations 1 and 2)}$$

$$\text{fraction of energy from carbohydrate oxidation} = \frac{\frac{w}{2} G^{s_g}}{F^{s_f} + \frac{w}{2} G^{s_g}}$$

where G represents the normalized plasma glucose concentration (e.g., plasma glucose concentration/5 mM), F represents the normalized plasma free fatty acid concentration (e.g., plasma free fatty acid concentration/500 µM), $s_g$ represents a metabolic parameter that characterizes the subject's responsiveness to a change in availability of carbohydrates, $s_f$ represents a metabolic parameter that characterizes the subject's responsiveness to a change in availability of fats, and w represents a metabolic parameter that characterizes the subject's predisposition or relative preference towards oxidation of carbohydrates or fats (a factor of ½ is included for convenience). In some instances, the metabolic parameters $s_g$ and $s_f$ can correspond to sensitivity parameters for carbohydrate oxidation and fat oxidation, respectively, and the metabolic parameter w can correspond to a weighting parameter that characterizes a genetic predisposition towards carbohydrate oxidation or fat oxidation.

For certain situations, it can be assumed that the brain oxidizes primarily carbohydrates, and Equations 1 and 2 can be used to describe the competition between carbohydrate oxidation and fat oxidation in remaining tissues. Letting B represent the fraction of total energy expenditure by the brain (e.g., approximately 0.15 under resting conditions), the following equation can be derived (see Appendix):

$$s_g \tilde{G} - s_f \tilde{F} + \log(w/2) = \log\left(\frac{RQ - 0.7 - 0.3B}{1 - RQ}\right) \quad \text{(Equation 3)}$$

where RQ represents the respiratory quotient, $\tilde{G}=\log G$, and $\tilde{F}=\log F$. Equation 3 is in a form that allows the application of regression analyses (e.g., least-squares analyses) to calculate values of the metabolic parameters $s_g$, $s_f$, and w based on the normalized plasma glucose concentration, the normalized plasma free fatty acid concentration, and the respiratory quotient.

Figure 2:
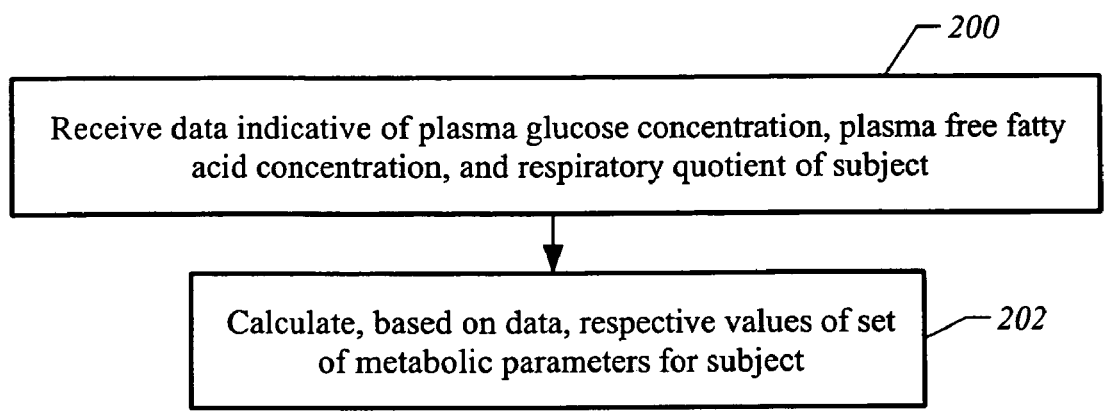
FIG. 2 illustrates a flow chart for assessing metabolic substrate utilization, according to an embodiment of the invention.

FIG. 2 illustrates a flow chart for assessing metabolic substrate utilization, according to an embodiment of the invention. At step 200, data indicative of the plasma glucose concentration, the plasma free fatty acid concentration, and the respiratory quotient of a subject is received. In the illustrated embodiment, the data includes a set of measurement results of the plasma glucose concentration, the plasma free fatty acid concentration, and the respiratory quotient of the subject, and a set of measurements is applied to the subject to produce the set of measurement results. The set of measurements can be applied using any of a number of functional, biochemical, and physical techniques appropriate to the set of measurement results being produced. In some instances, the set of measurements can include a set of clinical tests configured to measure the plasma glucose concentration, the plasma free fatty acid concentration, and the respiratory quotient of the subject. For example, the set of clinical tests can include biochemical analysis of a blood sample drawn from the subject to measure the plasma glucose concentration and the plasma free fatty acid concentration. The set of clinical tests can also include indirect calorimetric analysis of respiratory gases of the subject to measure the respiratory quotient.

In some instances, the set of measurements can include measurements that are applied at different measurement times. Thus, for example, the set of measurements can include a first set of measurements and a second set of measurements. The first set of measurements can be applied at a first measurement time to produce a first set of measurement results of the plasma glucose concentration, the plasma free fatty acid concentration, and the respiratory quotient at the first measurement time. The second set of measurements can be applied at a second measurement time to produce a second set of measurement results of the plasma glucose concentration, the plasma free fatty acid concentration, and the respiratory quotient at the second measurement time. In this example, the first measurement time is different from the second measurement time. To allow the application of regression analyses, it is desirable that one or more of the plasma glucose concentration, the plasma free fatty acid concentration, and the respiratory quotient undergo changes between different measurement times. Along this regard, the set of measurements can include measurements that are applied post-prandially, since values of the plasma glucose concentration and the plasma free fatty acid concentration can change considerably after a meal. Thus, for example, the set of measurements can include measurements that are applied based on a meal test, such as an OGTT.

At step 202, respective values of a set of metabolic parameters are calculated for the subject based on the data. In the illustrated embodiment, respective values of the metabolic parameters $s_g$, $s_f$, and w are calculated for the subject based on the set of measurement results of the plasma glucose concentration, the plasma free fatty acid concentration, and the respiratory quotient of the subject. In particular, the normalized plasma glucose concentration and the normalized plasma free fatty acid concentration are calculated based on the set of measurement results. Next, a regression analysis (e.g., a least-squares analysis) is performed to calculate the values of the metabolic parameters $s_g$, $s_f$, and w based on the normalized plasma glucose concentration, the normalized plasma free fatty acid concentration, and the respiratory quotient. In some instances, the values of the metabolic parameters $s_g$, $s_f$, and w can correspond to "optimized" values of the metabolic parameters $s_g$, $s_f$, and w (e.g., in a least-squares sense) based on fitting Equation 3 to the set of measurement results.

Advantageously, the illustrated embodiment can be used to identify characteristics of metabolic substrate utilization that typically cannot be identified based on simply measuring the respiratory quotient. In particular, the value of the metabolic parameter $s_g$ is indicative of the subject's responsiveness to a change in availability of carbohydrates, the value of the metabolic parameter $s_f$ is indicative of the subject's responsiveness to a change in availability of fats, and the value of the metabolic parameter w is indicative of the subject's predisposition towards oxidation of carbohydrates or fats. In such manner, the illustrated embodiment can provide information regarding the underlying causes of differences in carbohydrate oxidation and fat oxidation.

Applications of the Methodology

The methodology described herein can be used in numerous applications where metabolic substrate utilization plays a role. For example, the methodology can be used to develop a therapy for treating a metabolic disorder, such as obesity or diabetes. During a therapy discovery process, the methodology can be used to assess a candidate therapy to determine whether the candidate therapy has direct or indirect effects on metabolic substrate utilization. In particular, the methodology can be used to determine the extent to which changes in metabolic substrate utilization based on the candidate therapy are due to changes in metabolic substrate availability, changes in predisposition towards carbohydrate oxidation or fat oxidation, changes in responsiveness to availability of carbohydrates or fats, or a combination thereof. For example, it may be desirable to identify a candidate therapy that acts as a "switch" by shifting the balance between carbohydrate oxidation and fat oxidation. The methodology can be used to identify the candidate therapy as a "switch" based on determining whether the candidate therapy affects values of the metabolic parameters $s_g$, $s_f$, and w.

Subsequent to developing a therapy for treating a metabolic disorder, the methodology can be used to implement the therapy to treat the metabolic disorder. During a course of implementing the therapy, the methodology can be used to assess the therapy to determine whether the therapy has direct or indirect effects on metabolic substrate utilization. In particular, the methodology can be used to determine the extent to which changes in metabolic substrate utilization based on the therapy are due to changes in metabolic substrate availability, changes in predisposition towards carbohydrate oxidation or fat oxidation, changes in responsiveness to availability of carbohydrates or fats, or a combination thereof. For example, respective values of the metabolic parameters $s_g$, $s_f$, and w can be calculated for a subject during the course of implementing the therapy to determine how well the subject is responding to the therapy.

Figure 3:
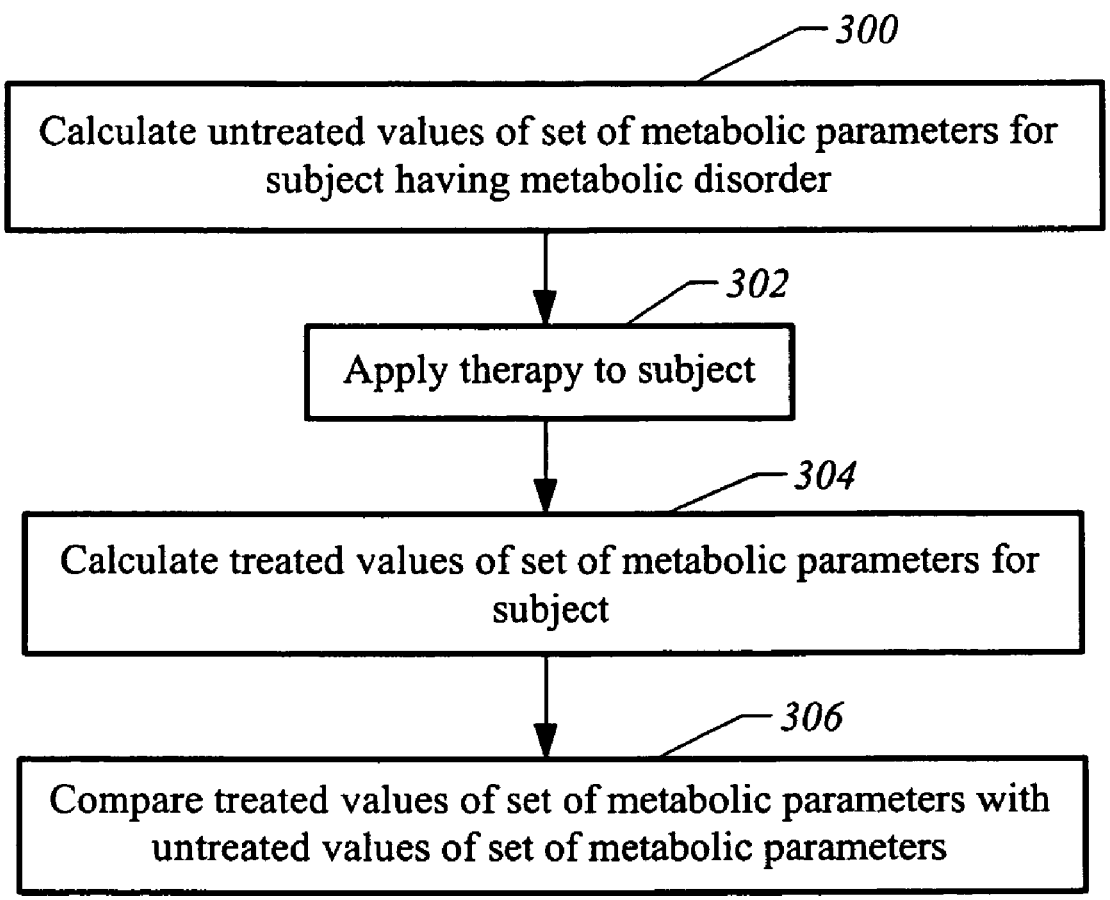
FIG. 3 illustrates a flow chart for assessing a therapy, according to an embodiment of the invention.

FIG. 3 illustrates a flow chart for assessing a therapy, according to an embodiment of the invention. At step 300, untreated values of a set of metabolic parameters are calculated for a subject having a metabolic disorder. Typically, the untreated values of the set of metabolic parameters are associated with a condition of the subject absent the therapy. In the illustrated embodiment, respective untreated values of the metabolic parameters $s_g$, $s_f$, and w are calculated for the subject based on a set of measurement results of the plasma glucose concentration, the plasma free fatty acid concentration, and the respiratory quotient of the subject prior to applying the therapy.

At step 302, the therapy is applied to the subject. The therapy can be applied using any of a number of techniques, such as orally, via inhalation, intravenously, or a combination thereof. Typically, a therapeutically effective dose of the therapy is applied to the subject. The therapeutically effective dose can be determined using any of a number of pharmacological techniques.

At step 304, treated values of the set of metabolic parameters are calculated for the subject. Typically, the treated values of the set of metabolic parameters are associated with a condition of the subject based on the therapy. In the illustrated embodiment, respective treated values of the metabolic parameters $s_g$, $s_f$, and w are calculated for the subject based on a set of measurement results of the plasma glucose concentration, the plasma free fatty acid concentration, and the respiratory quotient of the subject subsequent to applying the therapy.

At step 306, treated values of the set of metabolic parameters are compared with the untreated values of the set of metabolic parameters. In the illustrated embodiment, the treated values of the metabolic parameters $s_g$, $s_f$, and w are compared with the untreated values of the metabolic parameters $s_g$, $s_f$, and w. Typically, effectiveness of the therapy can be determined based on differences (if any) between the treated values of the metabolic parameters $s_g$, $s_f$, and w and the untreated values of the metabolic parameters $s_g$, $s_f$, and w. Thus, for example, based on a difference between the treated value of the metabolic parameter w and the untreated value of the metabolic parameter w, the therapy can be determined to be effective in terms of shifting the balance between carbohydrate oxidation and fat oxidation. As another example, based on a difference between the treated value of the metabolic parameter $s_g$ and the untreated value of the metabolic parameter $s_g$, the therapy can be determined to be effective in terms of altering the subject's responsiveness to a change in availability of carbohydrates. As a further example, based on a difference between the treated value of the metabolic parameter $s_f$ and the untreated value of the metabolic parameter $s_f$, the therapy can be determined to be effective in terms of altering the subject's responsiveness to a change in availability of fats.

As another example, the methodology can be used for diagnosing a metabolic disorder, such as obesity or diabetes. In particular, respective values of the metabolic parameters $s_g$, $s_f$, and w can be calculated for a subject based on a set of measurement results of the plasma glucose concentration, the plasma free fatty acid concentration, and the respiratory quotient of the subject. Next, the calculated values of the metabolic parameters $s_g$, $s_f$, and w can be compared with baseline values of the metabolic parameters $s_g$, $s_f$, and w. Typically, the baseline values of the metabolic parameters $s_g$, $s_f$, and w are associated with a condition absent a metabolic disorder, such as a healthy or a normal condition. For example, the baseline values of the metabolic parameters $s_g$, $s_f$, and w can each be about 1. The metabolic disorder can be diagnosed based on differences (if any) between the calculated values of the metabolic parameters $s_g$, $s_f$, and w and the baseline values of the metabolic parameters $s_g$, $s_f$, and w. Thus, for example, based on a difference between the calculated value of the metabolic parameter w and the baseline value of the metabolic parameter w, the subject can be diagnosed as having an imbalance between carbohydrate oxidation and fat oxidation. As another example, based on a difference between the calculated value of the metabolic parameter $s_g$ and the baseline value of the metabolic parameter $s_g$, the subject can be diagnosed as being under-responsive or over-responsive to a change in availability of carbohydrates. As a further example, based on a difference between the calculated value of the metabolic parameter $s_f$ and the baseline value of the metabolic parameter $s_f$, the subject can be diagnosed as being under-responsive or over-responsive to a change in availability of fats. It is contemplated that the methodology can be used as a diagnostic test implemented in a physician's office or clinic.

As another example, the methodology can be used for predicting effectiveness of a therapy for treating a metabolic disorder, such as obesity or diabetes. In particular, one or more of the metabolic parameters $s_g$, $s_f$, and w can serve as a biomarker of the therapy. Typically, correlation analysis is performed to determine whether one or more of the metabolic parameters $s_g$, $s_f$, and w are correlated with a particular response to the therapy, such as effectiveness of the therapy. For example, based on determining that a relatively larger value of the metabolic parameter w is correlated with a greater effectiveness of the therapy, the metabolic parameter w can be identified as a biomarker of the therapy. In some instances, correlation analysis can be performed based on one or more statistical tests. Statistical tests that can be used to identify correlation can include, for example, regression analysis and rank correlation test. In accordance with a particular statistical test, a correlation coefficient can be determined, and correlation can be identified based on determining that the correlation coefficient falls within a particular range or falls above or below a baseline value. Examples of correlation coefficients include goodness of fit statistical quantity $r^2$, coefficient of determination, and Spearman Rank Correlation coefficient $r_s$.

Once one or more of the metabolic parameters $s_g$, $s_f$, and w are identified as a biomarker of the therapy, such a biomarker can be used in numerous applications. For example, such a biomarker can be used to develop the therapy for treating the metabolic disorder. In particular, such a biomarker can be calculated for a subject to predict the degree of effectiveness of the therapy for that subject prior to a clinical trial. In such manner, such a biomarker can be used as an inclusion or exclusion criteria to select a group of subjects for the clinical trial, such that the clinical trial can target subjects that are likely to respond well to the therapy. Subsequent to developing the therapy, such a biomarker can be used to implement the therapy to treat the metabolic disorder. In particular, such a biomarker can be calculated for a subject to predict the degree of effectiveness of the therapy for that subject. In such manner, such a biomarker can be used by physicians to select subjects that are likely to respond well to the therapy.

As another example, the methodology can be used to classify subjects having a metabolic disorder, such as obesity or diabetes. In particular, respective values of the metabolic parameters $s_g$, $s_f$, and w can be calculated for each subject based on a set of measurement results of the plasma glucose concentration, the plasma free fatty acid concentration, and the respiratory quotient of that subject. Variability of values of the metabolic parameters $s_g$, $s_f$, and w across the subjects can be used to identify different subclasses of subjects. For example, one subclass of subjects can have relatively larger values of the metabolic parameter w, while another subclass of subjects can have relatively smaller values of the metabolic parameter w. Identification of these subclasses of subjects can be useful to determine which subjects may be more or less responsive to a therapy for treating the metabolic disorder. Also, variability of values of the metabolic parameters $s_g$, $s_f$, and w across the subjects can yield insights regarding possible defects in metabolic substrate utilization.

As another example, the methodology can be used to assess side effects of therapies, such as protease inhibitors for treating Acquired Immune Deficiency Syndrome ("AIDS"). In particular, respective treated values of the metabolic parameters $s_g$, $s_f$, and w can be calculated for a subject based on a set of measurement results of the plasma glucose concentration, the plasma free fatty acid concentration, and the respiratory quotient of the subject subsequent to applying a therapy. Next, the treated values of the metabolic parameters $s_g$, $s_f$, and w can be compared with baseline values of the metabolic parameters $s_g$, $s_f$, and w. Typically, the baseline values of the metabolic parameters $s_g$, $s_f$, and w are associated with a condition absent a side effect of the therapy. For example, the baseline values of the metabolic parameters $s_g$, $s_f$, and w can each be about 1. The side effect of the therapy can be identified based on differences (if any) between the treated values of the metabolic parameters $s_g$, $s_f$, and w and the baseline values of the metabolic parameters $s_g$, $s_f$, and w. Thus, for example, based on a difference between the treated value of the metabolic parameter w and the baseline value of the metabolic parameter w, the subject can be determined as having the side effect of the therapy.

As another example, the methodology can be used to design a regimen to allow improved metabolic performance in active subjects, such as athletes, firefighters, and soldiers. In particular, respective values of the metabolic parameters $s_g$, $s_f$, and w can be calculated for a subject based on a set of measurement results of the plasma glucose concentration, the plasma free fatty acid concentration, and the respiratory quotient of the subject. Next, a regimen can be designed for the subject based on the values of the metabolic parameters $s_g$, $s_f$, and w. Thus, for example, based on the value of the metabolic parameter w, the subject can be determined as having a predisposition towards carbohydrate oxidation, and a regimen can be designed based on the subject's predisposition (e.g., a diet including a large percentage of carbohydrates). In a similar fashion, the methodology can be used to design a regimen to facilitate weight loss. Also, the methodology can be used to assess metabolic substrate utilization in subjects having certain disorders, such as cancer and AIDS. For example, the methodology can be used to design a "rescue" regimen that can counteract the wasting effects of cancer or AIDS.

As a further example, the methodology can be used with computer models to gain insights regarding metabolic substrate utilization. For example, simulated values of the metabolic parameters $s_g$, $s_f$, and w can yield insights regarding which biological processes are associated with a metabolic disorder. As another example, simulated values of the metabolic parameters $s_g$, $s_f$, and w can yield insights regarding which biological processes modulate a response to a therapy for treating a metabolic disorder. Computer models can be defined as, for example, described in the following references: Paterson et al., U.S. Pat. No. 6,078,739; Paterson et al., U.S. Pat. No. 6,069,629; Paterson et al., U.S. Pat. No. 6,051,029; Thalhammer-Reyero, U.S. Pat. No. 5,930,154; McAdams et al., U.S. Pat. No. 5,914,891; Fink et al., U.S. Pat. No. 5,808,918; Fink et al., U.S. Pat. No. 5,657,255; Paterson et al., PCT Publication No. WO 99/27443; Paterson et al., PCT Publication No. WO 00/63793; Winslow et al., PCT Publication No. WO 00/65523; and Defranoux et al., PCT Publication No. WO 02/097706; the disclosures of which are incorporated herein by reference in their entirety. Also, computer models can be defined as, for example, described in the co-owned and co-pending patent application of Brazhnik et al., entitled "Method and Apparatus for Computer Modeling Diabetes," U.S. application Ser. No. 10/040,373, filed on Jan. 9, 2002 (U.S. Application Publication No. 20030058245, published on Mar. 27, 2003), the disclosure of which is incorporated herein by reference in its entirety. In addition, computer models can be implemented using commercially available computer models, including, for example, Entelos® Metabolism PhysioLab® systems.

EXAMPLES

The following examples are provided as a guide for a practitioner of ordinary skill in the art. The examples should not be construed as limiting the invention, as the examples merely provide specific implementations useful in understanding and practicing some embodiments of the invention.

Example 1

Tissue-specific versions of Equations 1 and 2 were developed for use with the metabolism PhysioLab® platform, which includes Entelos® Metabolism PhysioLab® systems (available from Entelos, Inc., Foster City, Calif.). These tissue-specific versions accounted for inter-tissue differences in metabolic substrate concentration and genetic predisposition. In some instances, these tissue-specific versions also accounted for metabolic substrates such as amino acids, lactates, and ketones. Values of tissue-specific versions of the metabolic parameters $s_g$, $s_f$, and w were calculated to predict carbohydrate oxidation rates and fat oxidation rates for different tissues under various meal and exercise protocols. Metabolic substrate oxidation rates for different tissues were then aggregated to predict metabolic substrate oxidation rates for an individual (e.g., "whole-body" metabolic substrate oxidation rates). Some results are shown in Table 1 given below.

tions 1 and 2 can be used to predict metabolic substrate oxidation rates for an individual under various conditions.

Example 2

Figure 4:
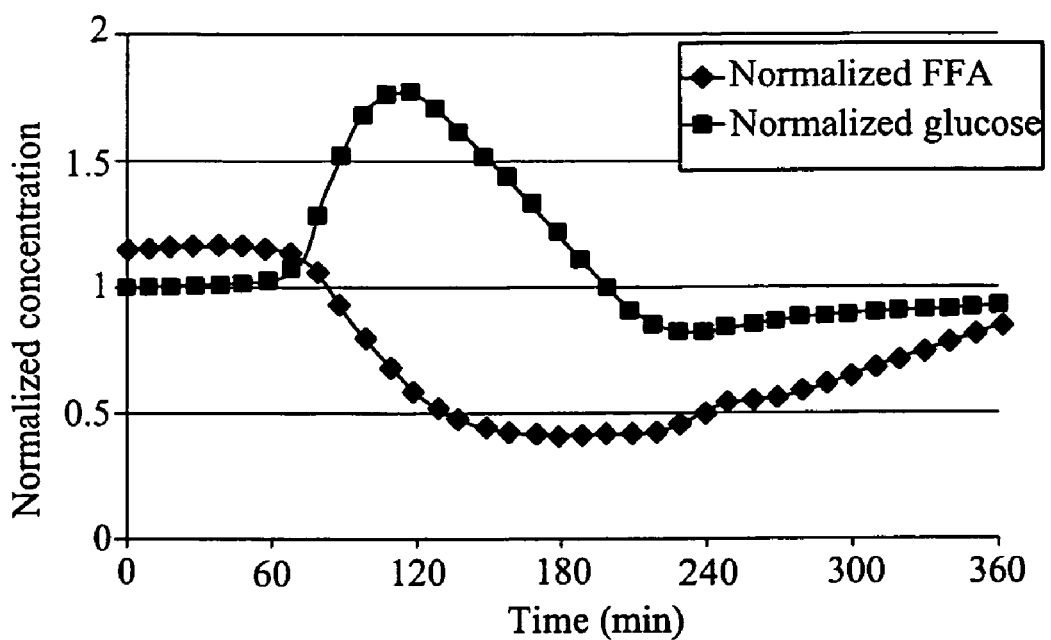
FIG. 4 illustrates simulated results for the normalized plasma free fatty acid concentration, the normalized plasma glucose concentration, and the respiratory quotient of a baseline virtual patient subjected to an oral glucose tolerance test ("OGTT"), according to an embodiment of the invention.
Figure 4:
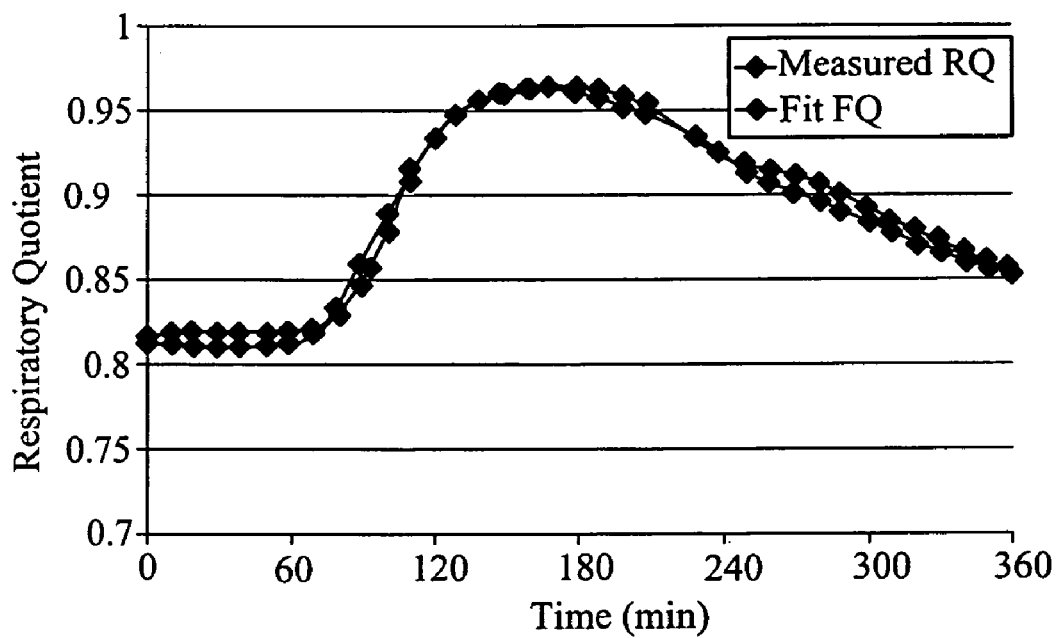

Equations 1, 2, and 3 were used to calculate values of the metabolic parameters $s_g$, $s_f$, and w based on a single meal test. The goal was to identify a relatively simple clinical test that allows values of the metabolic parameters $s_g$, $s_f$, and w to be calculated. Along this regard, an OGTT was simulated for a baseline virtual patient representing a 70 kg healthy individual. FIG. 4 illustrates simulated results for the normalized plasma free fatty acid concentration (labeled as "Normalized

TABLE 1

| Meal Protocol (CHO = carbohydrate) | Measured carbohydrate oxidation on last day (kcal) | Measured fat oxidation on last day (kcal) | Simulation carbohydrate oxidation on last day (kcal) | Simulation fat oxidation on last day (kcal) |
|---|---|---|---|---|
| 5 days; slightly positive energy balance; 48% CHO, 37% fat | 1163 ± 99 (Ref. 1) | 644 ± 67 (Ref. 1) | 1219 | 620 |
| 5 days; slightly positive energy balance; 35% CHO, 50% fat | 1051 ± 93 (Ref. 1) | 898 ± 44 (Ref. 1) | 886 | 888 |
| 7 days; energy balance; 45% CHO, 40% fat | 1218 ± 70 (Ref. 2) | 931 ± 80 (Ref. 2) | 1175 | 1025 |
| 7 days; energy balance; 60% CHO, 25% fat | 1530 ± 96 (Ref. 2) | 600 ± 96 (Ref. 2) | 1549 | 698 |
| 7 days; energy balance; 35% CHO, 50% fat | 910 ± 60 (Ref. 2) | 1240 ± 96 (Ref. 2) | 913 | 1248 |
| 1 day; +550 kcal energy balance; 52% CHO, 36% fat | 1177 ± 126 (Ref. 3) | 813 ± 157 (Ref. 3) | 1324 | 819 |

Ref. 1: Smith S R, de Jonge L, Zachwieja J J, Roy H, Nguyen T, Rood J C, Windhauser M M, and Bray G A, "Fat and carbohydrate balances during adaptation to a high-fat diet," Am. J. Clin. Nutr. 2000 Feb; 71(2): 450-457.
Ref. 2: Roy H J, Lovejoy J C, Keenan M J, Bray G A, Windhauser M M, and Wilson J K, "Substrate oxidation and energy expenditure in athletes and nonathletes consuming isoenergetic high- and low-fat diets," Am. J. Clin. Nutr. 1998 Mar; 67(3): 405-11.
Ref. 3: Poppitt S D, Livesey G, and Elia M, "Energy expenditure and net substrate utilization in men ingesting usual and high amounts of nonstarch polysaccharide," Am. J. Clin. Nutr. 1998 Oct; 68(4): 820-6.

The results shown in Table 1 include simulation results based on applying tissue-specific versions of Equations 1 and 2 to a baseline virtual patient created using the metabolism PhysioLab® platform. The baseline virtual patient was created using techniques as, for example, described in Paterson et al., U.S. Pat. No. 6,078,739; the co-pending and co-owned patent application to Paterson et al., entitled "Method and Apparatus for Conducting Linked Simulation Operations Utilizing A Computer-Based System Model", U.S. application Ser. No. 09/814,536, filed on Mar. 21, 2001 (U.S. Application Publication No. 20010032068, published on Oct. 18, 2001); and the co-pending and co-owned patent application to Paterson, entitled "Apparatus and Method for Validating a Computer Model", U.S. application Ser. No. 10/151,581, filed on May 16, 2002 (U.S. Application Publication No. 20020193979, published on Dec. 19, 2002); the disclosures of which are incorporated herein by reference in their entirety.

As shown in Table 1, the simulation results are compared to published results for healthy individuals. The ability to substantially reproduce the published results indicates that Equa- FFA"), the normalized plasma glucose concentration (labeled as "Normalized glucose"), and the respiratory quotient (labeled as "Measured RQ") of the baseline virtual patient subjected to the OGTT. As illustrated in FIG. 4, both the normalized plasma free fatty acid concentration and the normalized plasma glucose concentration change considerably in response to the OGTT. Changes in the normalized plasma free fatty acid concentration and the normalized plasma glucose concentration allowed values of the metabolic parameters $s_g$, $s_f$, and w to be readily calculated.

The simulated results were input into Equation 3, and a least-squares analysis was performed to calculate values of the metabolic parameters $s_g$, $s_f$, and w for the baseline virtual patient, which values are shown in Table 2. The values of the metabolic parameters $s_g$, $s_f$, and w for the baseline virtual patient were then used to calculate fitted values of the respiratory quotient based on Equation 3. The fitted values of the respiratory quotient were compared with simulated values of the respiratory quotient. As illustrated in FIG. 4, the fitted values of the respiratory quotient (labeled as "Fit RQ") substantially reproduced the simulated values of the respiratory quotient with a coefficient of determination of 0.98.

TABLE 2

|  | $s_g$ | $s_f$ | w |
|---|---|---|---|
| Baseline virtual patient | 0.8 ± 0.08 | 2.4 ± 0.05 | 1.03 ± 0.02 |
| Altered virtual patient | 0.43 ± 0.06 | 1.58 ± 0.03 | 1.26 ± 0.02 |

Figure 5:
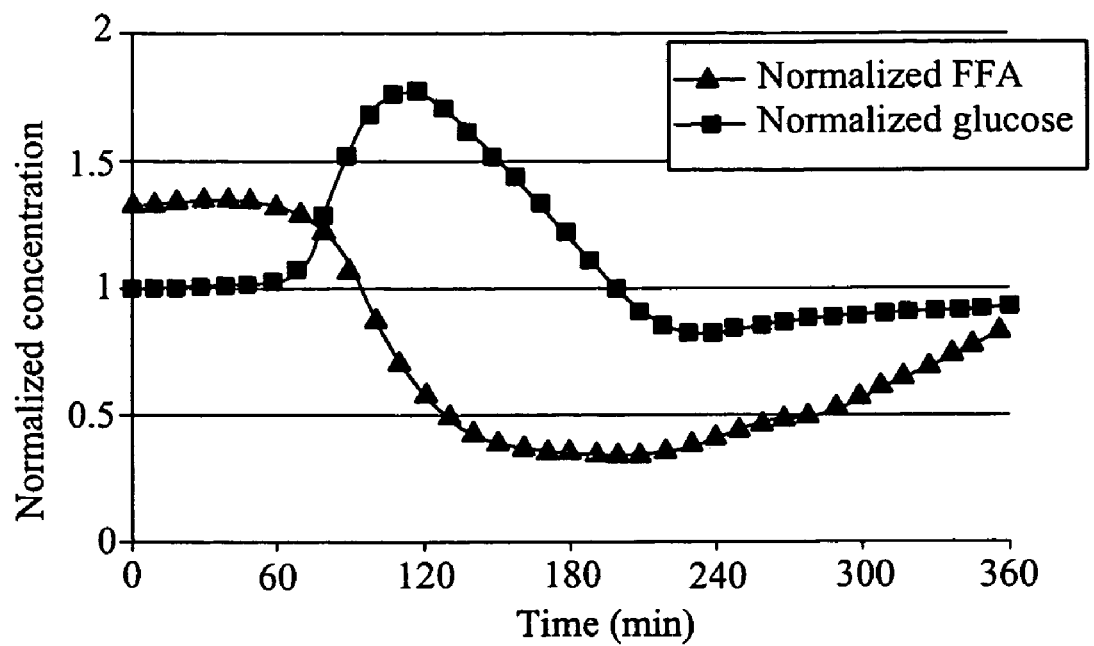
FIG. 5 illustrates simulated results for the normalized plasma free fatty acid concentration, the normalized plasma glucose concentration, and the respiratory quotient of an altered virtual patient subjected to an OGTT, according to an embodiment of the invention.
Figure 5:
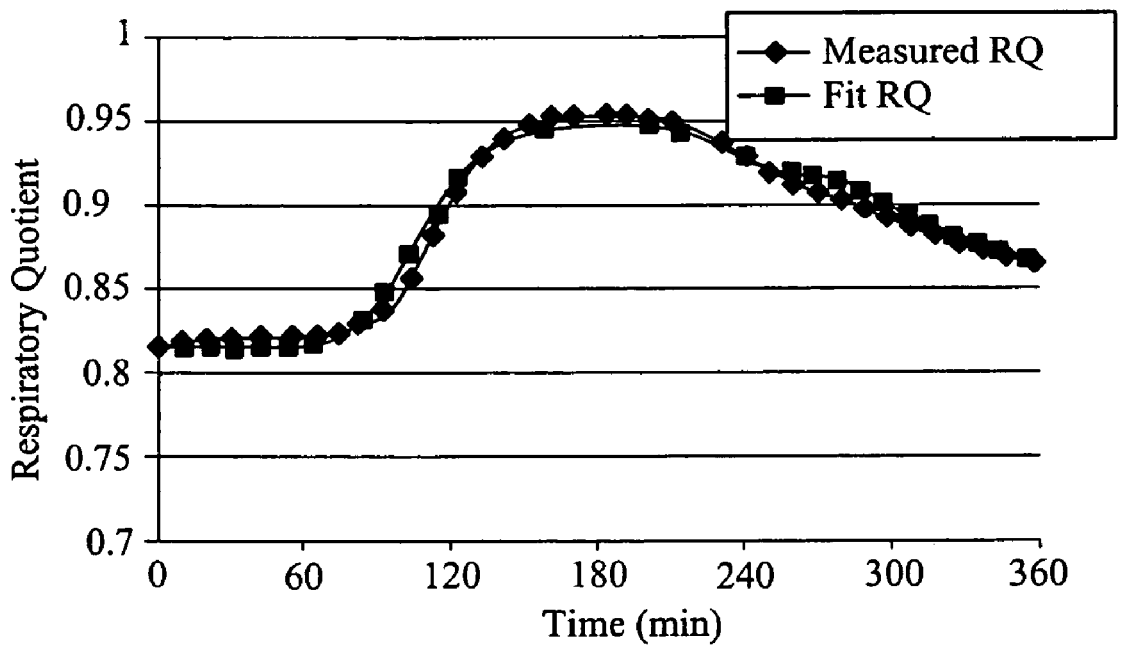

Next, it was determined whether differences in metabolic substrate utilization for different individuals can be identified using the metabolic parameters $s_g$, $s_f$, and w. Along this regard, the baseline virtual patient was altered to represent relatively subtle defects in metabolic substrate utilization in tissues other than the muscles and the brain. The resulting altered virtual patient represented an individual that is less prone to fat oxidation in the basal state, and is less responsive to changes in glucose concentration and free fatty acid concentration than a healthy individual. FIG. 5 illustrates simulated results for the normalized plasma free fatty acid concentration (labeled as "Normalized FFA"), the normalized plasma glucose concentration (labeled as "Normalized glucose"), and the respiratory quotient (labeled as "Measured RQ") of the altered virtual patient subjected to an OGTT. The simulated results were input into Equation 3, and a least-squares analysis was performed to calculate values of the metabolic parameters $s_g$, $s_f$, and w for the altered virtual patient, which values are shown in Table 2. As shown in Table 2, the values of the metabolic parameters $s_g$, $s_f$, and w for the altered virtual patient are substantially different from the values of the metabolic parameters $s_g$, $s_f$, and w for the baseline virtual patient. In addition, the values of the metabolic parameters $s_g$, $s_f$, and w for the altered virtual patient are consistent with the imposed subtle defects in metabolic substrate utilization. Thus, this example indicates that the imposed subtle defects in metabolic substrate utilization can be readily identified using the metabolic parameters $s_g$, $s_f$, and w. The values of the metabolic parameters $s_g$, $s_f$, and w for the altered virtual patient were then used to calculate fitted values of the respiratory quotient based on Equation 3. The fitted values of the respiratory quotient were compared with simulated values of the respiratory quotient. As illustrated in FIG. 5, the fitted values of the respiratory quotient (labeled as "Fit RQ") substantially reproduced the simulated values of the respiratory quotient with a coefficient of determination of 0.98.

Figure 6:
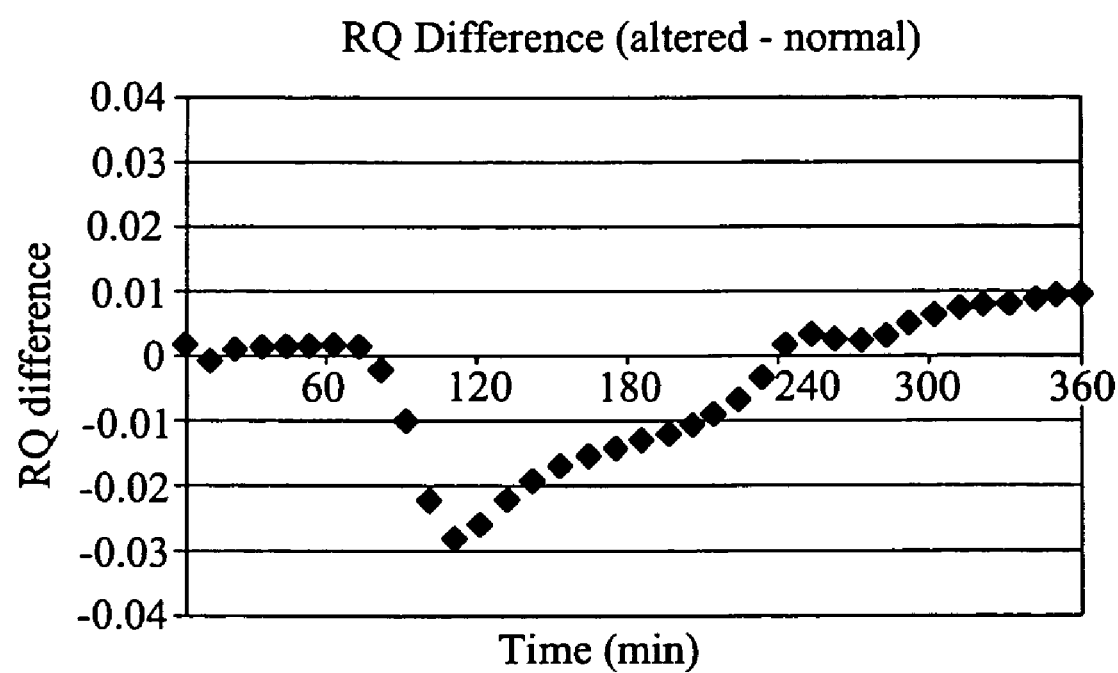
FIG. 6 illustrates differences in simulated values of the respiratory quotient of a baseline virtual patient and an altered virtual patient, according to an embodiment of the invention.

To determine whether the imposed subtle defects in metabolic substrate utilization can be detected using simply measurements of the respiratory quotient, a plot of differences in simulated values of the respiratory quotient for the baseline virtual patient and the altered virtual patient was generated as illustrated in FIG. 6. In view of the typical experimental error associated with measurements of the respiratory quotient (e.g., approximately ±0.02), FIG. 6 indicates that a statistically significant difference between the two virtual patients cannot be detected using simply measurements of the respiratory quotient.

In a similar fashion as described above, it was determined that the metabolic parameters $s_g$, $s_f$, and w can be used to distinguish the baseline virtual patient from virtual patients representing individuals with insulin resistance and diabetes.

Example 3

Equations 1, 2, and 3 were used to calculate values of the metabolic parameters $s_g$, $s_f$, and w based on published studies. The published studies included measurements of the plasma free fatty acid concentration, the plasma glucose concentration, and the respiratory quotient at several measurement times after a meal. One published study included measurements for individuals under three different meal protocols, namely glucose only, a high fat meal, and a mixed meal (Bobbioni-Harsch E, Habicht F, Lehmann T, James R W, Rohner-Jeanrenaud, and Golay A, "Energy expenditure and substrate oxidative patterns, after glucose, fat or mixed load in normal weight subjects," Eur. J. Clin. Nutr. 1997 June;51(6): 370-4). Another published study included measurements for individuals following OGTT (Bulow J, Simonsen L, Wiggins D, Humphreys S M, Frayn K N, Powell D, and Gibbons G F, "Co-ordination of hepatic and adipose tissue lipid metabolism after oral glucose," J. Lipid Res. 1999 November;40(11): 2034-43). Results from the published studies were used to calculate values of the metabolic parameters $s_g$, $s_f$, and w for the individuals who participated in the published studies.

Along this regard, certain issues were addressed:

1. Results from the published studies were sometimes reported at every hour or every half-hour, which is less frequent than results typically available from simulation.
2. In the published study by Bobbioni-Harsch et al., values of the respiratory quotient were reported as averages over 1 hour intervals, while plasma glucose concentration and plasma free fatty acid concentration were measured at beginnings and ends of these 1 hour intervals.
3. Effects of insulin on muscle glucose uptake and other time delays can result in measured values of the respiratory quotient remaining elevated for some time period after glucose concentration and free fatty acid concentration return to basal values.
4. Results from the published studies typically show average values of measurements across a group of individuals rather than values for each individual of the group.

To account for differences in frequency at which measurements were applied and for the time delays, "effective" values of the normalized plasma glucose concentration and "effective" values of the normalized plasma free fatty acid concentration were used in Equation 3. These "effective" values were weighted averages of current values and those at previous measurement times. Values at previous measurement times were included in the calculations to represent the effect of interstitial insulin in increasing muscle glucose uptake and, hence, carbohydrate oxidation. Interstitial insulin concentration in the muscles typically lags plasma concentration by about 60 minutes (Sjostrand M, Gudbjomsdottir S, Holmang A, Lonn L, Strindberg L, and Lonnroth P, "Delayed transcapillary transport of insulin to muscle interstitial fluid in obese subjects," Diabetes 2002 September;51(9):2742-8). Therefore, a value of the plasma glucose concentration at 60 minutes in the past was included to determine a current value of the respiratory quotient. For the published study by Bobbioni-Harsch et al., the following weighted average was used to calculate an "effective" value of the normalized plasma glucose concentration:

$$RQ = \frac{3G_{beginning} + 3G_{end} + 2G_{t-60}}{8}, \quad \text{(Equation 4)}$$

effective value at the time the $RQ$ was reported where $G_{beginning}$ represents the normalized plasma glucose concentration at the beginning of the 1 hour interval, $G_{end}$ represents the normalized plasma glucose concentration at the end of the 1 hour interval, and $G_{t-60}$ represents the normalized plasma glucose concentration at 60 minutes before the 1 hour interval. This weighted average was chosen to estimate an average value of the normalized plasma glucose concentration during the 1 hour interval (using the $G_{beginning}$ and $G_{end}$ terms) and to provide a representation of the time-delayed effects described above (using the $G_{t-60}$ term). A similar calculation was performed to calculate an "effective" value of the normalized plasma free fatty acid concentration at each measurement time. These "effective" values of the normalized plasma glucose concentration and the normalized plasma free fatty acid concentration were then used in Equation 3 to calculate values of the metabolic parameters $s_g$, $s_f$, and w.

Figure 7:
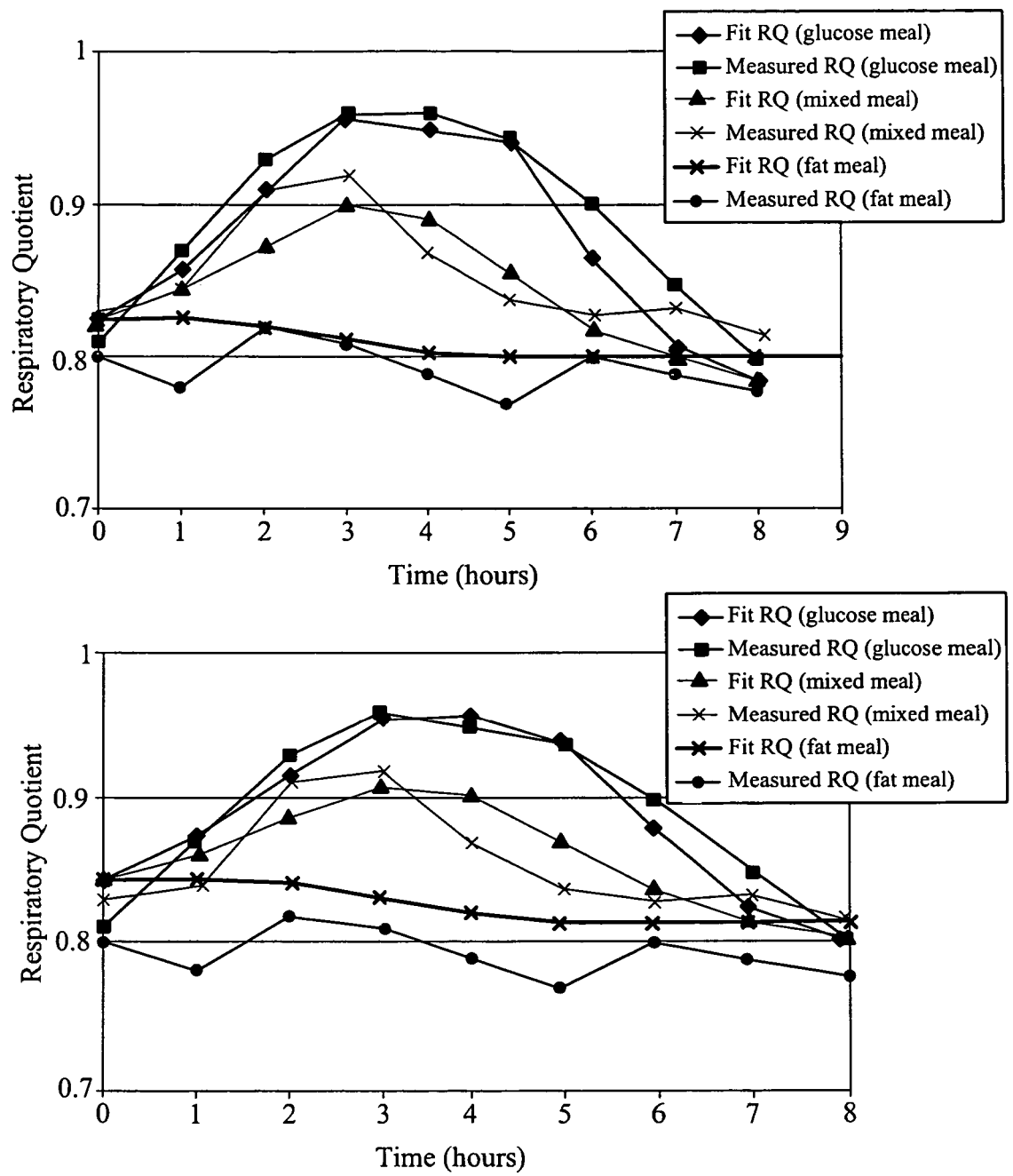
FIG. 7 illustrates fitted values and reported values of the respiratory quotient for individuals subjected to three different meal protocols, according to an embodiment of the invention.

Bobbioni-Harsch et al. reported measurements for 10 healthy individuals under three different meal protocols. Values of the metabolic parameters $s_g$, $s_f$, and w were calculated using results from the glucose only meal protocol and using combined results for all three meal protocols. The values of the metabolic parameters $s_g$, $s_f$, and w are shown in Table 3. Values of the metabolic parameters $s_g$, $s_f$, and w for the glucose only meal protocol and for all three meal protocols were also used to calculate fitted values of the respiratory quotient based on Equation 3. FIG. 7 illustrates reported values of the respiratory quotient along with fitted values of the respiratory quotient calculated using values of the metabolic parameters $s_g$, $s_f$, and w for the glucose only meal protocol (top graph) and for all three meal protocols (bottom graph). As illustrated in FIG. 7, the fitted values of the respiratory quotient substantially reproduced the reported values of the respiratory quotient.

TABLE 3

| Data Used | $s_g$ | $s_f$ | w |
|---|---|---|---|
| Glucose meal | 0.9 ± 0.8 | 1.2 ± 0.2 | 1.3 ± 0.2 |
| All three meals | 1.1 ± 0.9 | 1.4 ± 0.2 | 1 ± 0.1 |

A similar procedure was used to calculate values of the metabolic parameters $s_g$, $s_f$, and w based on measurements for individuals following OGTT as reported by Bulow et al. The values of the metabolic parameters $s_g$, $s_f$, and w are shown in Table 4. These values are similar to those obtained from the results reported by Bobbioni-Harsch et al. and confirm the applicability of the metabolic parameters $s_g$, $s_f$, and w to characterize healthy individuals.

TABLE 4

| Data Used | $s_g$ | $s_f$ | w |
|---|---|---|---|
| OGTT | 0.8 ± 0.5 | 1.2 ± 0.2 | 1.0 ± 0.1 |

As described above, results from the published studies typically show average values of measurements across a group of individuals rather than values for each individual of the group. As a result, the values of the metabolic parameters $s_g$, $s_f$, and w were calculated for an "average" individual rather than for a particular individual. It is contemplated that similar calculations can be performed for different individuals who participated in the published studies to determine variability of values of the metabolic parameters $s_g$, $s_f$, and w across the different individuals.

Example 4

While multiple measurements applied post-prandially can sometimes provide a more informative characterization of metabolic substrate utilization, it can also be useful to calculate a value of a single metabolic parameter based on overnight fasted measurements of the plasma glucose concentration, the plasma free fatty acid concentration, and the respiratory quotient. It is contemplated that this single metabolic parameter can serve as a fasting index to discriminate between different groups of individuals and, potentially, between different individuals.

Equation A-1 in the Appendix can be rewritten as:

$$w = 2\left(\frac{RQ - 0.7 - 0.3B}{1 - RQ}\right)\frac{F^{s_f}}{G^{s_g}}. \quad \text{(Equation 5)}$$

In view of the values of the metabolic parameters $s_g$ and $s_f$ calculated from post-prandial studies in healthy individuals, it can be assumed that the values of the metabolic parameters $s_g$ and $s_f$ are equal to 1, and the value of the metabolic parameter w (which serves as the fasting index) can be calculated using overnight fasted measurements as follows:

$$w = 2\left(\frac{RQ - 0.7 - 0.3B}{1 - RQ}\right)\frac{F}{G}. \quad \text{(Equation 6)}$$

Typical overnight fasted values for a healthy individual include: B≈0.15; F≈1; G≈1; and RQ≈0.83. Inputting these typical values in Equation 6 gives w≈1.0. Thus, individuals with a greater predisposition towards carbohydrate oxidation will typically have w>1, and individuals with a greater predisposition towards fat oxidation will typically have w<1. The expected experimental uncertainty for the metabolic parameter w can be represented as:

$$\frac{\Delta w}{w} = \sqrt{\left(\frac{0.3(1-B)\Delta RQ}{(1-RQ)(RQ-0.7-0.3B)}\right)^2 + \left(\frac{\Delta F}{F}\right)^2 + \left(\frac{\Delta G}{G}\right)^2}, \quad \text{(Equation 7)}$$

where $\Delta G$, $\Delta F$, and $\Delta RQ$ represent experimental uncertainties associated with measurements of the plasma glucose concentration, the plasma free fatty acid concentration, and the respiratory quotient, respectively. Typically, the first uncertainty term can be the dominant term, and the following equation can be used as an approximation of the expected experimental uncertainty:

$$\frac{\Delta w}{w} \approx \frac{0.3(1-B)\Delta RQ}{(1-RQ)(RQ-0.7-0.3B)}. \quad \text{(Equation 8)}$$

Using typical overnight fasted values (RQ=0.83 and ΔRQ=0.02), the expected experimental uncertainty for the metabolic parameter w is about 35%.

To determine whether the metabolic parameter w can be used to discriminate between groups of individuals, ratios of the metabolic parameter w were calculated for pairwise comparisons of: (1) lean, healthy control individuals; (2) obese, diabetic individuals before bariatric surgery; and (3) post-obese, diabetic individuals 30 months after bariatric surgery that resulted in significant weight loss and normalization of glucose and free fatty acid concentrations. If a ratio is greater than 1, a group represented in the numerator typically has a greater predisposition towards carbohydrate oxidation. On the other hand, if the ratio is less than 1, the group represented in the numerator typically has a greater predisposition towards fat oxidation.

The following ratios were calculated based on results from a published study (Benedetti G, Mingrone G, Marcoccia S, Benedetti M, Giancaterini A, Greco A V, Castagneto M, and Gasbarrini G, "Body composition and energy expenditure after weight loss following bariatric surgery," J. Am. Coll. Nutr. 2000 April;19(2):270-4):

$$w_C/w_{OD}=1.07\pm0.4,$$

$$w_C/w_{POD}=0.15\pm0.05,$$

$$w_{POD}/w_{OD}=7.0\pm2.3,$$

where $w_C$, $w_{OD}$, and $w_{POD}$ represent the metabolic parameter w for the control individuals; the obese, diabetic individuals; and the post-obese, diabetic individuals, respectively. The ratios do not indicate a significant difference in metabolic substrate utilization between the obese, diabetic individuals and the control individuals, but indicate a significant shift in predisposition towards carbohydrate oxidation in the obese, diabetic individuals following weight loss via bariatric surgery. It has been hypothesized that reduced levels of plasma free fatty acid following bariatric surgery is responsible for the increased predisposition towards carbohydrate oxidation. However, since the metabolic parameter $w_{POD}$ already accounts for changes in plasma free fatty acid concentration, it is likely that another factor may be responsible for the increased predisposition towards carbohydrate oxidation in post-obese, diabetic patients following bariatric surgery.

An embodiment of the invention relates to a computer storage product including a processor-readable medium having processor-executable code thereon for performing various processor-implemented operations. The term "processor-readable medium" is used herein to include any medium that is capable of storing or encoding a sequence of instructions or codes for performing the methods described herein. The media and code may be those specially designed and constructed for the purposes of the invention, or they may be of the kind well known and available to those having skill in the computer software arts. Examples of processor-readable media include, but are not limited to: magnetic media such as hard disks, floppy disks, and magnetic tape; optical media such as CD-ROMs and holographic devices; magneto-optical media such as floptical disks; carrier waves signals; and hardware devices that are specially configured to store and execute program code, such as application-specific integrated circuits ("ASICs"), programmable logic devices ("PLDs"), read only memories ("ROMs"), random access memories ("RAMs"), erasable programmable read only memories ("EPROMs"), and electrically erasable programmable read only memories ("EEPROMs"). Examples of processor-executable code include machine code, such as produced by a compiler, and files containing higher-level code that are executed by a computer using an interpreter. For example, an embodiment of the invention may be implemented using Java, C++, or other object-oriented programming language and development tools. Additional examples of processor-executable code include encrypted code and compressed code.

Moreover, an embodiment of the invention may be downloaded as a computer program product, where the program may be transferred from a remote computer (e.g., a server) to a requesting computer (e.g., a client) by way of data signals embodied in a carrier wave or other propagation medium via a communication link (e.g., a modem or network connection). Accordingly, as used herein, a carrier wave can be regarded as a processor-readable medium.

Another embodiment of the invention may be implemented in hardwired circuitry in place of, or in combination with, computer-executable code.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the invention has been described with reference to the specific embodiments thereof, it should be understood by those skilled in the art that various changes may be made and equivalents may be substituted without departing from the true spirit and scope of the invention as defined by the claims. In addition, many modifications may be made to adapt a particular situation, material, composition of matter, method, process operation or operations, to the spirit and scope of the invention. All such modifications are intended to be within the scope of the claims. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

APPENDIX

Derivation of Equation 3

The respiratory quotient for fat oxidation is typically 0.7, and the respiratory quotient for carbohydrate oxidation is typically 1.0. Thus, the non-protein portion of the respiratory quotient can be represented as:

$$RQ = \frac{0.7 \times \text{fat oxidation rate} + 1.0 \times \text{carbohydrate oxidation rate}}{\text{fat oxidation rate} + \text{carbohydrate oxidation rate}}. \quad \text{(A-1)}$$

For certain situations, it can be assumed that the brain primarily oxidizes carbohydrates and that the fraction of the total energy expenditure by the brain is B (and hence the fraction of total energy expenditure by remaining tissues is (1−B)). Using these assumptions and substituting Equations 1 and 2 into the above equation gives:

$$RQ = 1.0 * B + (1-B)\frac{0.7F^{S_f} + 1.0*(w/2)G^{S_g}}{F^{S_f} + (w/2)G^{S_g}} \quad (A\text{-}2)$$

$$= B + (1-B)\left(1 - \frac{0.3F^{S_f}}{F^{S_f} + (w/2)G^{S_g}}\right)$$

or $$RQ = 1 - \frac{0.3(1-B)F^{S_f}}{F^{S_f} + (w/2)G^{S_g}}.$$

Equation (A-2) can be rewritten as:

$$(w/2)G^{S_g} = \left(\frac{RQ - 0.7 - 0.3B}{1 - RQ}\right)F^{S_f}. \quad (A\text{-}3)$$

After taking logarithms of both sides of Equation (A-3), one obtains:

$$\log(w/2) + s_g \log(G) = \log\left(\frac{RQ - 0.7 - 0.3B}{1-RQ}\right) + s_f \log(F), \quad (A\text{-}4)$$

which is the same as Equation 3.

What is claimed is:

1. A processor-readable medium, comprising:
   code to receive data indicative of a blood glucose level, a blood free fatty acid level, and a respiratory quotient of a subject; and
   code to calculate, based on the data, a value of a metabolic parameter for the subject, the value of the metabolic parameter being indicative of whether the subject has a predisposition towards one of carbohydrate oxidation and fat oxidation.

2. The processor-readable medium of claim 1, wherein the data includes a first set of measurement results and a second set of measurement results, the first set of measurement results being indicative of the blood glucose level, the blood free fatty acid level, and the respiratory quotient of the subject at a first measurement time, the second set of measurement results being indicative of the blood glucose level, the blood free fatty acid level, and the respiratory quotient of the subject at a second measurement time, the first measurement time being different from the second measurement time.

3. The processor-readable medium of claim 1, wherein the code to calculate the value of the metabolic parameter includes code to perform a regression analysis on the data.

4. The processor-readable medium of claim 1, further comprising: code to compare the value of the metabolic parameter with a baseline value.

5. The processor-readable medium of claim 1, wherein the metabolic parameter is a first metabolic parameter, the processor-readable medium further comprising:
   code to calculate, based on the data, a value of a second metabolic parameter for the subject, the value of the second metabolic parameter being indicative of the subject's responsiveness to a change in carbohydrate availability.

6. The processor-readable medium of claim 1, wherein the metabolic parameter is a first metabolic parameter, the processor-readable medium further comprising:
   code to calculate, based on the data, a value of a second metabolic parameter for the subject, the value of the second metabolic parameter being indicative of the subject's responsiveness to a change in fat availability.

7. A computer-implemented method, comprising:
   applying a set of measurements to a subject to produce a set of measurement results for the subject, the set of measurements being configured to evaluate a blood glucose level, a blood free fatty acid level, and a respiratory quotient of the subject;
   based on the set of measurement results, using a computer to determine whether the subject has a predisposition towards one of carbohydrate oxidation and fat oxidation; and
   displaying the determination on a user-interface.

8. The method of claim 7, wherein the set of measurements is configured to measure the blood glucose level, the blood free fatty acid level, and the respiratory quotient of the subject after an overnight fast.

9. The method of claim 7, wherein the set of measurements includes a first set of measurements and a second set of measurements, the first set of measurements being configured to measure the blood glucose level, the blood free fatty acid level, and the respiratory quotient of the subject at a first measurement time, the second set of measurements being configured to measure the blood glucose level, the blood free fatty acid level, and the respiratory quotient of the subject at a second measurement time, the first measurement time being different from the second measurement time.

10. The method of claim 7, wherein the determining whether the subject has the predisposition includes applying a regression analysis on the set of measurement results.

11. The method of claim 7, wherein the determining whether the subject has the predisposition includes:
    based on the set of measurement results, calculating a value of a metabolic parameter of the subject, the value of the metabolic parameter being indicative of whether the subject has the predisposition; and
    comparing the value of the metabolic parameter with a baseline value.

12. The method of claim 7, further comprising:
    based on the set of measurement results, determining the subject's responsiveness to a change in carbohydrate availability.

13. The method of claim 7, further comprising:
    based on the set of measurement results, determining the subject's responsiveness to a change in fat availability.

14. The method of claim 7, further comprising:
    based on whether the subject has the predisposition, diagnosing a metabolic disorder of the subject.

15. The method of claim 7, further comprising:
    based on whether the subject has the predisposition, selecting a therapy for the subject.

16. The method of claim 7, further comprising:
    based on whether the subject has the predisposition, selecting the subject for a clinical trial of a therapy.

* * * * *

UNITED STATES PATENT AND TRADEMARK OFFICE
CERTIFICATE OF CORRECTION

| | | |
|---|---|---|
| PATENT NO. | : 7,654,955 B2 | Page 1 of 1 |
| APPLICATION NO. | : 10/995030 | |
| DATED | : February 2, 2010 | |
| INVENTOR(S) | : Polidori et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this

Twenty-third Day of November, 2010

David J. Kappos
*Director of the United States Patent and Trademark Office*